United States Patent [19]

Atkinson et al.

[11] Patent Number: 5,154,499

[45] Date of Patent: Oct. 13, 1992

[54] MEDICAL/SURGICAL FLUID DELIVERY DEVICE WITH MULTI-FUNCTIONAL HANDLE

[75] Inventors: Robert W. Atkinson, Dover; Michael J. Laco, Sherrodsville; William J. Donizetti, Dover, all of Ohio

[73] Assignee: Zimmer, Inc., Warsaw, Ind.

[21] Appl. No.: 793,309

[22] Filed: Nov. 14, 1991

Related U.S. Application Data

[63] Continuation-in-part of Ser. No. 514,080, Apr. 25, 1990, abandoned.

[51] Int. Cl.⁵ .............................................. A47B 95/02
[52] U.S. Cl. .................................... 312/244; 248/286; 128/66; 16/340; 403/91; 403/98
[58] Field of Search ............... 312/244, 245; 248/286, 248/287, 133; 128/65, 66; 16/339, 340, 345, 348, 375, 376; 403/91, 98, 116, 117

[56] References Cited

U.S. PATENT DOCUMENTS

| | | |
|---|---|---|
| D. 214,606 | 7/1969 | Best, Jr. . |
| D. 276,934 | 12/1984 | Smallhorn . |
| D. 286,435 | 10/1986 | Atkinson . |
| D. 292,527 | 10/1987 | Bullock et al. . |
| D. 298,460 | 11/1988 | Pryor . |
| 1,693,169 | 11/1928 | Young .................................. 16/348 |
| 2,558,955 | 7/1951 | Hilton ............................. 312/244 X |
| 2,897,034 | 7/1959 | Kalen .............................. 312/244 X |
| 2,966,257 | 12/1960 | Littlejohn ....................... 312/244 X |
| 3,033,508 | 5/1962 | Prohaska ............................. 248/286 |
| 3,185,233 | 5/1965 | Provi ............................... 312/244 X |
| 3,194,164 | 7/1965 | Fink et al. . |
| 3,910,266 | 10/1975 | Kawase . |
| 3,912,168 | 10/1975 | Mullins et al. . |
| 3,993,054 | 11/1976 | Newman . |
| 4,140,296 | 2/1974 | Guzman Guillen ............ 248/286 X |
| 4,557,725 | 12/1985 | Heyne et al. . |
| 4,561,431 | 12/1985 | Atkinson . |
| 4,635,621 | 1/1987 | Atkinson . |
| 4,655,197 | 4/1987 | Atkinson . |
| 4,879,798 | 11/1989 | Petre . |

FOREIGN PATENT DOCUMENTS

2189998B 11/1987 United Kingdom .

OTHER PUBLICATIONS

Stryker Surgical brochure–Orthotec Pulsatile Lavage System–The Clear Choice–1986.
Zimmer, Inc. brochure–Zimmer Low Pressure Irrigation System–Lit. No. 97-5175-08 Rev 1-1985.
Zimmer, Inc. brochure–Pulsavac Wound Debridement System–Lit. No. 97-5150-08 Rev 1-1987.
Zimmer, Inc.–1987 Catalog section J for Wound Care Products–pp. ii, J1, J3–Lit. No. 97-5000-115.
Zimmer, Inc.–1987 Catalog section G for Arthroscopy–pp. ii, G21, G32–Lit. No. 97-5000-112.

*Primary Examiner*—James R. Brittain
*Assistant Examiner*—Brian K. Green
*Attorney, Agent, or Firm*—Margaret L. Geringer

[57] ABSTRACT

The present invention comprises a housing which includes a handle assembly attached thereto. The handle assembly has a first retracted position and a second extended position. The handle assembly includes a fluid container suspension mechanism thereon. Accordingly, when the handle assembly is in the second extended position, fluid containers may be suspended from the suspension mechanism on the handle assembly. The handle assembly may be retracted to the first position for storage or transport or for carrying the device via the handle assembly.

1 Claim, 3 Drawing Sheets

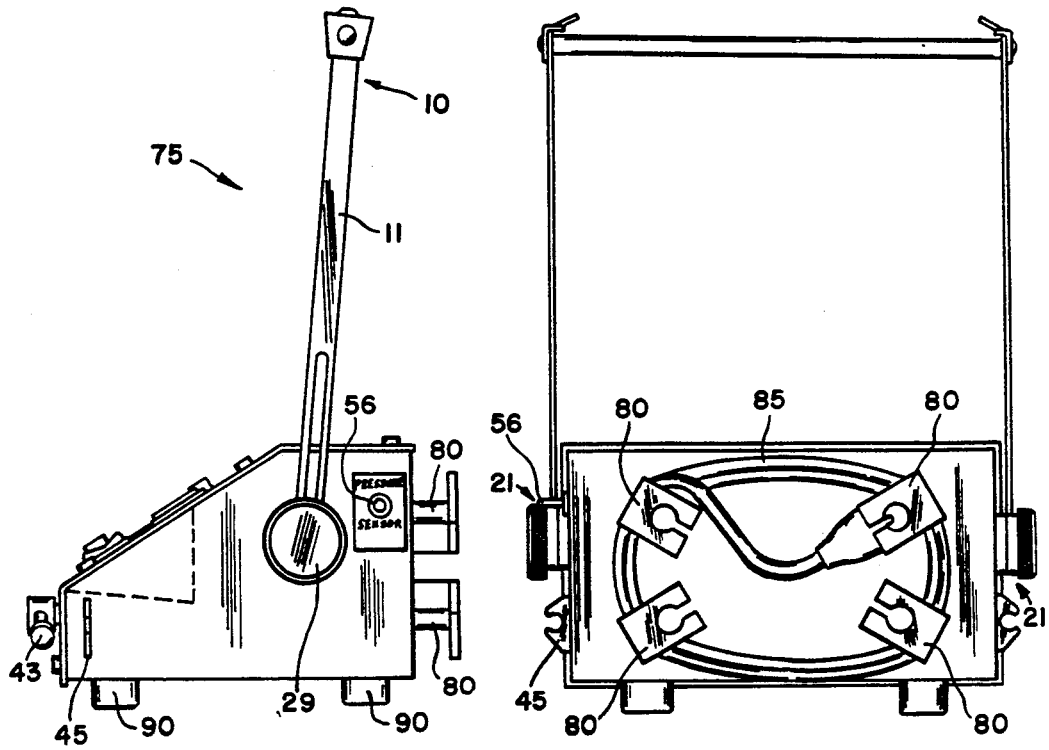
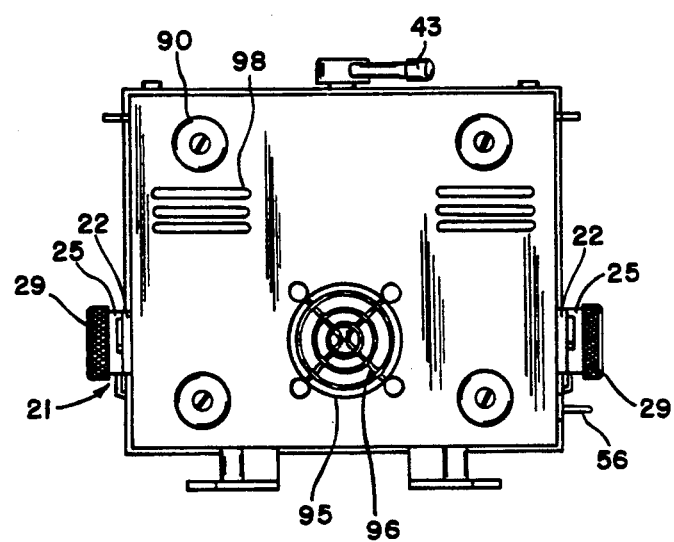

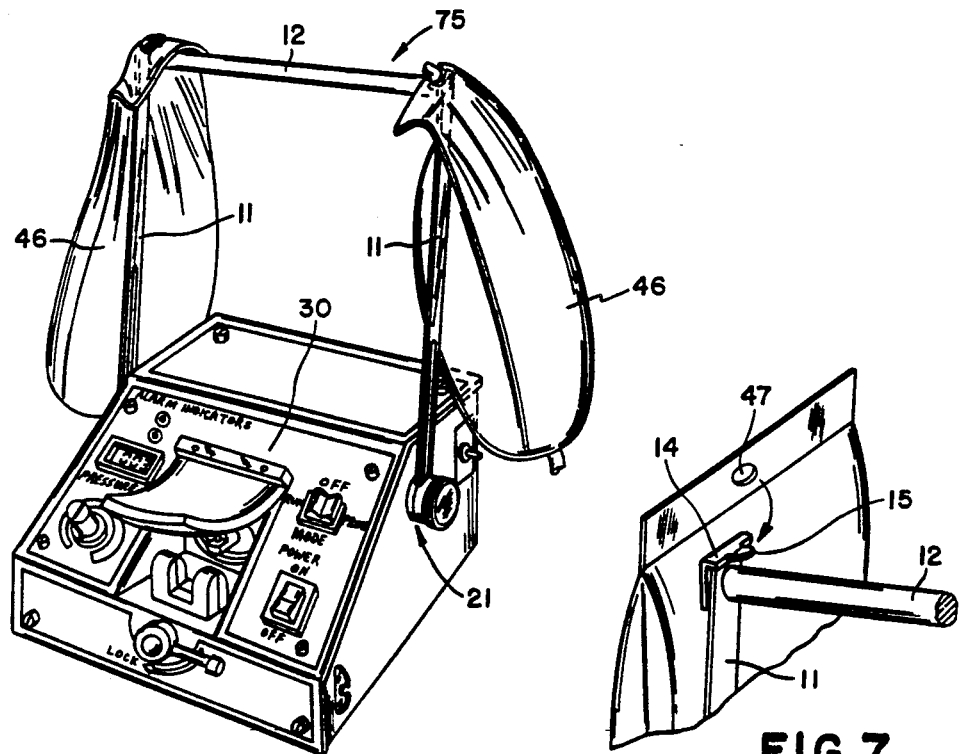
FIG. 6
FIG. 7
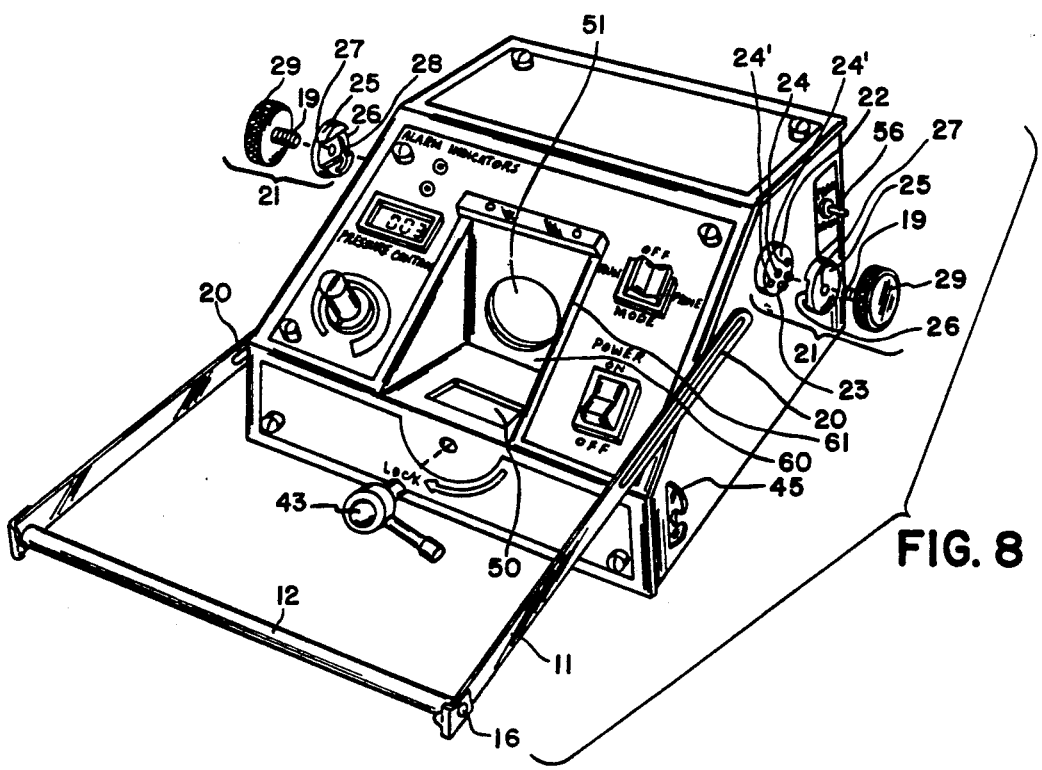
FIG. 8

5,154,499

MEDICAL/SURGICAL FLUID DELIVERY DEVICE WITH MULTI-FUNCTIONAL HANDLE

This application is a continuation-in-part of Applic. Ser. No. 07/514,080 filed Apr. 25, 1990, now abandoned.

BACKGROUND OF THE INVENTION

The present invention relates to medical/surgical fluid delivery devices, and particularly to such devices which utilize fluid suspension bags/containers in conjunction therewith. This invention is particularly suitable for fluid pumping devices for use with various types of endoscopy procedures, or for lavage-type fluid delivery applications; however its use is not limited thereto.

Heretofore, fluid delivery devices which utilize fluid suspension bags typically are suspended from fluid suspension poles such as disclosed in the following:

U.S. Pat. No. 3,993,054 to Newman discloses a lavage device which is placed on bench 108 and which utilizes two fixed support hangars 109 which are attached to bench 108 to suspend liquid supply containers 111.

U.S. Pat. No. 3,912,168 to Mullins et al. discloses an irrigation lavage unit including a handle 52 on the housing which allows the unit to be carried in its normal orientation. The unit further provides a bracket on the rear for the power cord to be wrapped around.

Stryker Surgical provides various lavage or irrigation units such as the Surgilav 201 or the Ortholav 202 which include handles such as the type shown in U.S. Pat. No. 3,912,168. Stryker Surgical also provides a lavage unit called the Orthotec 203 which includes a collapsible handle which collapses into the housing to allow storage of materials on top of the unit when collapsed or to allow convenient carrying for transport.

U.S. Pat. No. 4,557,725 to Heyne et al. discloses an IV pump cassette 12 of the type for use in delivering IV fluids to a patient at a controlled rate. This pump cassette is received in a recessed chamber 14 in the front of a driver mechanism for connection to a motor.

U.S. Pat. Nos. 4,561,431; 4,635,621; and 4,655,197 to Atkinson disclose a lavage system in which the housing 11 is mounted on a movable floor stand from which a supply 15 of fluid may be suspended. The pumps, such as 51A and 51B, are held within pump housings 68A and 68B, respectively, by a pump support. Doors 74A and 74B cooperate to secure the pumps in the respective pump housing.

U.S. Pat. No. D 214,606 to Best, Jr. discloses a design for an ultrasonic nebulizer comprising what is apparently a pump unit on the front of a handled housing, the housing having a solution support attached to its rear wall.

U.S. Pat. No. D 276,934 to Smallhorn discloses a combined pump and telescopic support pole design wherein the support pole extends from the top of the pump. This support pole appears to extend and collapse.

U.S. Pat. No. D 298,460 to Pryor discloses a design for an IV bottle hanger in which the pole appears to be vertically adjustable.

OBJECTS OF THE INVENTION

A principal object of this invention is to provide a fluid delivery device which is portable and easily carried via a handle, and wherein the carrying handle may also be utilized for suspending fluid containers or bags therefrom.

Another object of the invention is to provide a fluid delivery device with a multi-functional handle which may be used as a carrying handle while in a retracted or lowered position and which may be used for suspending fluid containers therefrom while in an extended or raised position.

A further object of the invention is to provide such a multi-functional handle in which the retracted position and the extended position of the handle may be at different angular orientations to the fluid delivery device housing.

A still further object of the invention is to provide such a fluid delivery device which includes a recess for receiving a fluid delivery pump in which the recess includes a flexible guard at least partially covering the opening to the recess.

SUMMARY OF THE INVENTION

The present invention provides a fluid delivery device which is portable and easily carried via a handle while the handle is in a first, lowered or retracted position. The handle serves a multi-functional purpose, and has a raised or extended position in which fluid containers may be suspended from an extending hook or prong on the handle. This multi-functional handle provides a portable fluid delivery device which is convenient to transport, convenient to use, and which provides built-in fluid suspension capabilities, preventing the need for the separate fluid suspension poles or stands which tend to be more cumbersome. Thus, the present invention could be easily adapted for use in an emergency room or in an emergency medical service vehicle where a more compact, easy to transport, fluid delivery device with fluid suspension capabilities would be beneficial, although its use is not limited to such circumstances.

BRIEF DESCRIPTION OF THE DRAWINGS

The features and objects of the invention, as well as others, will become apparent to those skilled in the art by referring to the accompanying drawings:

FIG. 3 is a side elevational view of the device of FIG. 2;

FIG. 4 a rear elevational view of the device of FIG. 2;

FIG. 5 is a plan view of the device of FIG. 2;

FIG. 6 is a perspective view of the device of FIG. 1 with the handle shown in the extended position and with fluid bags suspended therefrom;

FIG. 7 is an enlarged partial view taken at circle "C" of FIG. 6; and

FIG. 8 is a partially exploded perspective view of the device of FIG. 1.

DETAILED DESCRIPTION OF THE INVENTION

Figure 1:
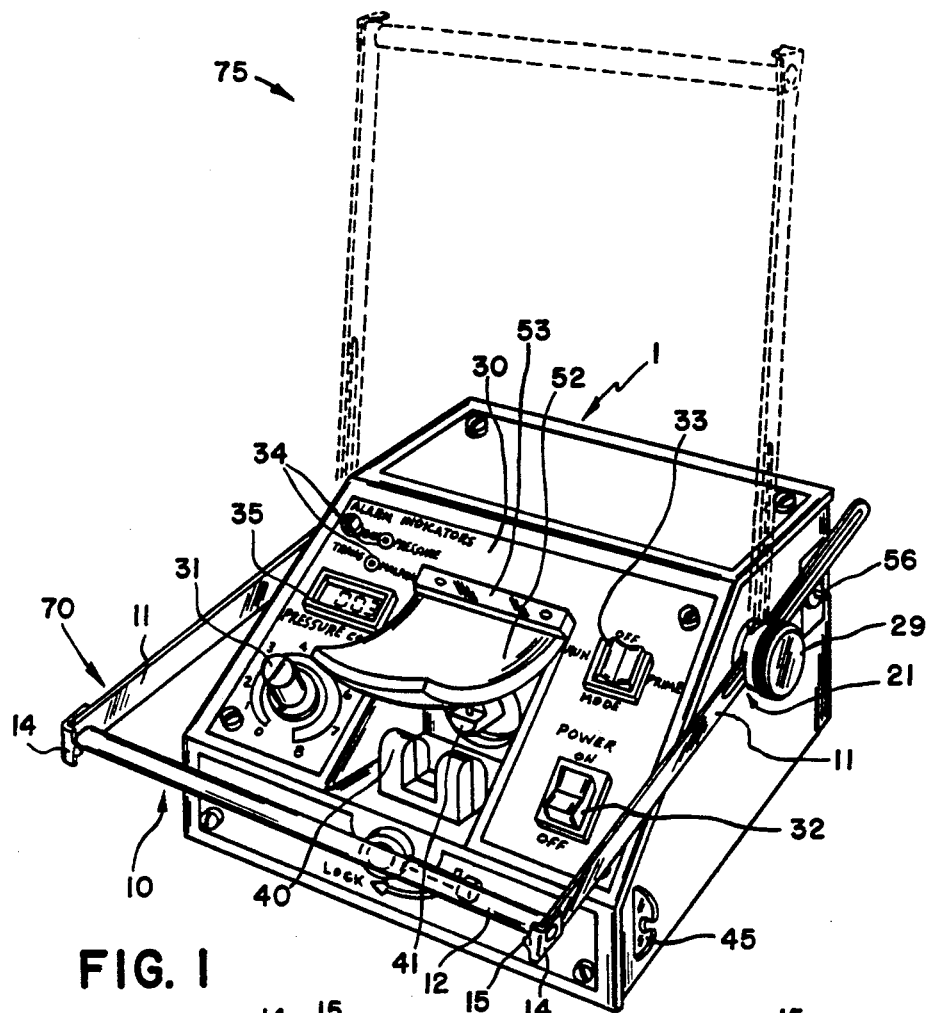
FIG. 1 is a perspective view of a fluid delivery device according to the present invention with the handle shown in the lowered or retracted position and with the extended handle position shown in phantom lines.
Figure 2:
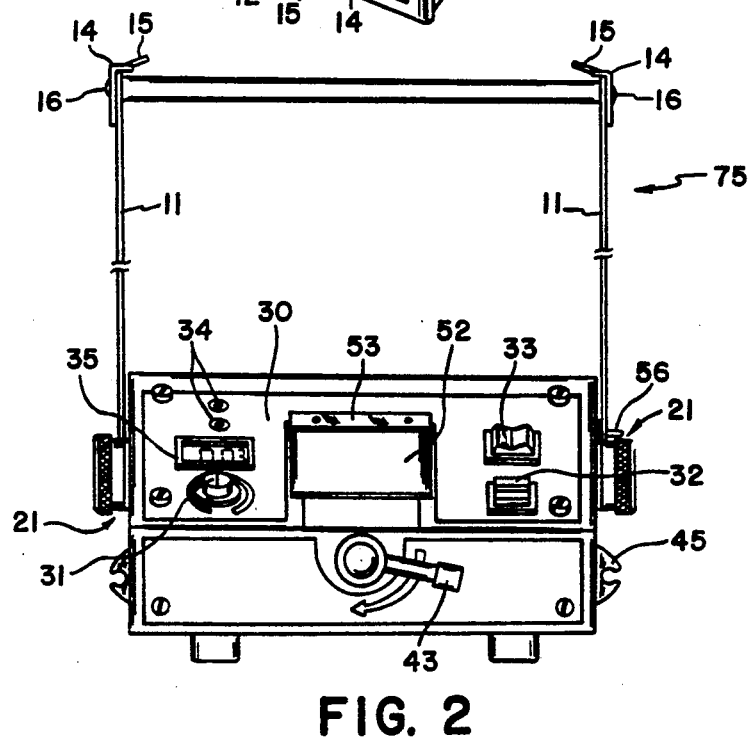
FIG. 2 is a front elevational view of the device of FIG. 1 with the handle shown in the extended position.

FIGS. 1–8 illustrate a particularly advantageous embodiment of a medical/surgical fluid delivery device according to the present invention. The fluid delivery device includes a housing 1 with a handle assembly 10 attached thereto. The handle assembly 10 is shown in a first retracted or lowered position 70 in FIGS. 1 and 8, and it is shown in a second extended or raised position 75 in FIGS. 2-7, and also in FIG. 1 in phantom lines. The first position 70 of the handle assembly 10 is particularly suitable for use a carrying handle for conveniently transporting or moving the fluid delivery device. The second position 75 of the handle assembly 10 is particularly suitable and adapted for use as a fluid container support. The handle assembly 10 includes fluid container suspension members, such as solution bag clips 14 which include extending prongs 15 for fitting into a holder hole 47 in solution bags 46, such as shown in FIGS. 6 and 7. It is understood that any other means for suspending fluid containers (besides the clips 14), may be utilized to suspend the fluid containers or solutions bags 46 from the handle assembly 10.

As shown in FIG. 1, the first position 70 is lowered from the extended position 75 in a vertical direction with respect to the bottom of the fluid delivery device 1, and is also pivoted, such that the angular orientation of the first position 70 with respect to the housing 1 is different from the angular orientation of the second position 7 with respect to the housing 1. The first position 70 may suitably be approximately parallel to the bottom surface of the fluid delivery device as shown in FIG. while the second position 75 may suitably be rotated approximately 90° to 100° from the first position 70.

The handle assembly 10 of the preferred embodiment shown, includes two side supports connected by a cross-piece 12. Screws 16 may be used to conveniently secure the solution bag clip 14 to each side support 11 and the side supports 11 then to the cross-piece 12 of the handle assembly 10. The side supports 11 each include an elongated slot 20 therein. The handle assembly is connected to the housing 1 on both sides by a handle adjustment mechanism 21 which connects to each side support 11. The adjustment mechanism 21 enables the handle assembly position to be adjusted or moved when the adjustment mechanism 21 is in a loosened or adjustment position, and firmly secures the handle assembly position in the desired location/position when the adjustment mechanism 21 is in a tightened or secured position.

The adjustment mechanism 21 on each side of the housing 1 includes a solution bracket locator plate 22, a solution bracket retainer plate 25, and a solution bracket adjustment knob 29. The adjustment knob 29 may be knurled for easier gripping. The adjustment knob 29 includes an extending threaded pin 19 which connects through the central threaded hole 27 on retainer plate 25, through slot 20 in side support 11, and through the central threaded hole 24 on locator plate 22. The locator plates 22 are each secured to the respective side of the housing 1 by two screws (not shown) through side threaded holes 24' on locator plate 22 which may be secured by nuts (not shown) on the inside of the housing 10. Each retainer plate 25 includes a groove 26 for locating the respective side support 11 therein. The slot 20 in each side support 11 is slidable along the respective pin 19 which is extending therethrough when the respective adjustment mechanism 21 is in the loosened position, and is not slidable along the respective pin 19 when the adjustment mechanism is in the tightened position. The adjustment mechanism 21 is in the tightened position when the adjustment knob 29 is threaded securely in all the way to securely tighten the knob 29 to the retainer plate 25 to the side support 11 to the locator plate 22 to prevent relative movement therebetween. Each adjustment mechanism 21 is in the loosened position when each threaded adjustment knob 29 is respectively unthreaded or backed off just enough to enable the side supports to slide along the slots 20 to adjust the position of the handle assembly 10. A stop mechanism, such as a prepositioned nut (not shown) may be utilized on the end of pin 19 (inside the housing) to prevent the knob 29 from backing out too far, and thus causing the adjustment mechanism 21 to inadvertently disassemble while the knob 29 is being loosened to change the handle position. On the other hand, it may be desirable to not include such a stop to enable the handle assembly 10 to be removed without getting inside the housing 1. The inclusion or not of such a stop is a matter of design choice.

The position of locator plates 22 is secured to or fixed relative to housing 1. However, when the knobs 29 are loosened, knobs 29, retainer plates 25, and side, supports 11 may be rotated with respect to the housing 10. The locator plate 22 may include one or more protruding pins 23 which align with curved recessed slot 28 in retainer plate 25. The pins 23 cooperate with curved slot 28 to provide limits or stops to the rotation of the handle assembly 10. This enables controlled angular adjustment of the handle assembly 10 when the knobs 29 are loosened. When the knobs 29 are loosened, and the side supports 11 are extended the fixed pins 23 can glide/slide in alignment with curved slot 28 as the position of the retainer plate 25 and side support 11 are rotated to change the position of the handle assembly 10, as desired. Thus when pins 23 and corresponding slot 28 are provided on the adjustment mechanism 21, in order to move the handle assembly 10 from the lowered, retracted position 70 to the raised, extended position 75, the side supports 11 must be extended in order to rotate the handle assembly. The side supports 11 must be extended to an extent such that the pins 23 will be outside of the end tip of side supports 11 when the handle assembly is rotated. Accordingly, to move the handle assembly from lowered position 70 to extended position 75, the adjustment mechanism is loosened and then the side supports are first extended and then the handle assembly is rotated. The adjustment mechanism is then tightened. When moving from position 75 to 70, the adjustment mechanism is loosened and then the handle assembly is first rotated and then the side supports 11 are collapsed or retracted. When pins 23 and slot 28 are provided, and the adjustment mechanism 21 is loosened, the side supports 11 can slide in groove 26 in the lowered position 70, but the side supports must be substantially fully extended to rotate the handle assembly and must remain in this substantially fully extended position when the handle assembly is in the raised position 75. When rotating the handle assembly 10 to the upright position 75, the handle assembly 10 is rotated until pins 23 contact one end of the slot 28, at which time rotation will be limited or stopped by this contact, thus providing a preferred angular orientation for the upright position 75 of the handle assembly 10. When rotating the handle assembly 10 to the lowered position 70, the handle assembly 10 is rotated until pins 23 contact the opposite end of slot 28, at which time rotation will be limited or stopped by this contact, thus providing a preferred angular orientation for the lowered position 70 of the handle assembly 10 (different from the angular orientation for the upright position as shown by FIG. 1). To secure the handle assembly 10 in the desired position, and to prevent further rotation of the handle assembly 10, the adjustment mechanism 21 is tightened when the desired position is reached. As seen in FIG. 3, the pins 23 and cooperating slot 28 can be designed so that the handle assembly 10 may be rotated to slightly past the vertical or perpendicular position (relative to the bottom of the housing 1). This position, as shown in FIG. 3, is advantageous for supporting the weight of the suspended fluid containers 46.

As shown in FIGS. 2-6, the housing 1 may include a first set of feet 90 on the bottom side of the housing 1 and a second set of feet 80 on the rear side of the housing. The feet 90 and 80 may be attached to the housing by screws or other suitable means. The housing 1 generally rests on feet 90 for operation of the fluid delivery device. When the handle assembly 10 is in the retracted carrying position 70, the housing 1 can be set down on feet 80, when picking up and setting down housing 1 for transportation. The FIGS. do not show the housing resting on feet 80.

The feet 80 may be slightly elongated or extended feet to enable an elongated power cord (extending from rear of housing as shown in FIG. 4) to be wrapped thereabout. The bottom side of housing 1, as shown in FIG. 5 illustrates a vent hole 95 and covering grate 96 which provide venting for a fan (inside the housing, and not shown). Other vents 98 may also be provided to help release heat from the motor (inside the housing, and not shown).

The motor and other components inside the housing may be set up as desired to achieve the desired fluid delivery functions, and are not part of the present claimed invention. In conjunction with this, the angled control panel face 30 may have any desired arrangement of controls/functions for operating the fluid delivery device in the desired manner. The control panel face 30 shown, includes a pressure adjustment knob 31, pressure indicator readout 35, alarm indicators 34, a mode switch 33, and a power switch 32.

As shown in FIG. 6, the solution or fluid bags 46 are suspended from solution clips 14 by locating prongs 15 through holder holes 47 in solution bags 46. The solution bag 46 may be connected via tubing (not shown) to a suitable fluid delivery pump (not shown) which would be located in pump cavity 60 in housing 1. The pump may be similar to the pump shown in Atkinson's U.S. Pat. No. 4,635,621 as irrigation pump 51A, although is not limited thereto. The pump would be located on pump connector bracket 41 and pump holder bracket 40 which extend through openings 51 and 50, respectively, in housing 1. The pump would be connected to a motor (not shown) inside the housing 1 via pump connector bracket 41. A flexible guard 52 extends over a portion of the opening 61 to cavity 60. The flexible guard 52 allows easy access to cavity 60 for positioning or removing the pump by simply lifting the guard 52 as shown in FIG. 1. The flexible guard is secured to housing 1 by bracket 53 which is positioned over the top edge of guard 52 and is screwed through guard 52 and into housing 1. The guard 52 may be made from any suitable flexible plastic material or other suitable flexible material, and may be clear or translucent or opaque, as desired. The flexible nature of guard 52 enables the pump to be easily loaded and unloaded by merely lifting the guard, and alleviates the need for more complicated closure mechanisms, such as hinged doors. The guard 52 helps to keep dust or other articles out of the pump cavity 60. The guard 52 is shown in a raised position in FIGS. 1 and 6, and is shown down on the housing 1 in FIG. 2.

The housing 1 further includes a pump lock lever 43 for locking and unlocking the fluid delivery pump into cavity/recess 60. The lever 43 is operatively connected to pump holder bracket 40 such that when the pump is placed on brackets 40 and 41 and then lever 43 is rotated to the lock position, this causes the split in bracket 40 to widen and thus secures the pump onto bracket 40 by spreading bracket 40 out to tighten it against the flanges on pump (such as the type pump shown in Atkinson's U.S. Pat. No. 4,635,621). Any suitable mechanism can be used to effect the spreading action via lever 43. The pump would then be operatively connected to a suitable fluid delivery outlet such as a lavage handpiece (not shown), or any other suitable fluid delivery outlet for endoscopic use or other medical/surgical fluid delivery use as is known in the art. It is also known to provide a pressure sensor connector, such as 56, for connection, via tubing, with the fluid delivery system. The tubing (not shown) of the fluid delivery system may be secured to housing 1 via tubing clips 45, as desired, to help keep the tubing orderly.

The fluid delivery device of the present invention may be stored or transported with the handle assembly in the first retracted position 70. Upon removing the device from storage, the device may be placed on a flat, tabletop type surface. Then, the adjustment mechanism 21 may be loosened and the handle assembly extended along slots 20 and rotated to the upright second position 75. The adjustment mechanism is then tightened to secure the position of the handle assembly. Fluid/solution bags 46 may then be suspended from clips 14 on handle assembly 10. A fluid pump 42 may be secured in cavity 60 and connected operatively to the fluid bags 46 and to the rest of the fluid delivery system, as desired.

The fluid delivery device may be manufactured and assembled by any suitable means and in any convenient manner. Any suitable materials may be utilized. The side supports 11, clips 14, and cross-piece 12 may be metal to provide the necessary strength to support the weight of the fluid bags 46; however, any materials strong enough to support the fluid bags 46 and strong enough to support the weight of the housing 1 when the device is being carried may be utilized.

It is readily seen that this invention provides a fluid delivery device which is portable and easily carried via a handle, and wherein the carrying handle may also be extended and utilized for suspending fluid containers therefrom. While this invention has been described and exemplified in terms of a particularly advantageous embodiment, those skilled in the art can appreciate that modifications can be made without departing from the spirit and scope of this invention.

We claim:

1. A method of utilizing a medical/surgical fluid delivery device in which the device includes a housing and a handle means attached thereto, the handle means having an adjustment means which allows the handle means to move between a first retracted position and a second extended position, and wherein the handle means includes a fluid container suspension means thereon, the steps comprising:
   a) storing the device with the handle means in the first, retracted position;
   b) removing the device from storage;
   c) carrying the device by the handle means to a desired location with the handle means in the first retracted position;
   d) moving the handle means from the first retracted position to the second extended position; and
   e) handing at least one fluid container from the fluid container suspension means while the handle means is in the second extended position.

* * * * *